US00PP11322P

United States Patent [19]

Hanson

[11] Patent Number: Plant 11,322

[45] Date of Patent: Apr. 4, 2000

[54] *ACER×FREEMANII* MAPLE TREE NAMED 'SIENNA'

[76] Inventor: Bradley K. Hanson, 550 Robert Ct., Mahtomedi, Minn. 55115

[21] Appl. No.: 08/978,255

[22] Filed: Nov. 25, 1997

[51] Int. Cl.[7] ..... A01H 5/00

[52] U.S. Cl. ..... Plt./224

[58] Field of Search ..... Plt./53.6, 224

[56] References Cited

U.S. PATENT DOCUMENTS

P.P. 7,655 9/1991 Wandell ..... Plt./224

OTHER PUBLICATIONS

*Ace×freemanii* Maples listed in Frank J. Schmidt Wholesale Sales Catalog, 1 page (Apr. 1997–1998).

*Acer×freemanii* Maples listed in Bailey Nursery Wholesale Catalog, 1 page (Jun., 1995–1996).

*Acer rubrum×A. saccharinum* "Autumn Blaze" Maple, advertisement in trade publication, American Nurseryman, 1 page (Jan. 1997).

*Acer freemanii* "Autumn Delight Maple" listed in Robinson Nursery Catalog, p. 9 (May 1997–1998).

*Acer×freemanii* "Armstong Maple," listed in Bailey Nursery Wholesale Catalog, p. 36 (Jun. 1995–1996).

*Acer×freemanii* "Jeffersred Autumn Blaze® Maple," listed in Bailey Nursery Wholesale Catalog, p. 36 (Jun. 1995–1996).

*Acer×freemanii* "Celzam Celebration® Maple," listed in Bailey Nursery Wholesale Catalog, p. 37 (Jun. 1995–1996).

*Acer×freemanii* "Scarsen Scarlet Sentinel® Maple," listed in Bailey Nurseries, Inc., St. Paul, MN, p. 37 (Jun. 1995–1996).

*Primary Examiner*—Howard J. Locker
*Assistant Examiner*—Anne Marie Grünberg
*Attorney, Agent, or Firm*—Merchant & Gould P.C.

[57] ABSTRACT

A novel variety of *Acer×freemanii* was discovered in Minnesota. It has a distinct upright, pyramidal shape, vibrant deep burgundy fall color and superior winter hardiness.

6 Drawing Sheets

BACKGROUND OF THE INVENTION

Colorful maple varieties are desirable ornamental shade trees in various regions of the United States. One of the most popular shade trees in the Midwest, Mid central and Intermountain regions is an *Acer×freemanii* (*A. Ruhrum×A. Saccharinum*) named 'Autumn Blaze' (U.S. Plant Pat. No. 4,864). This tree exhibits a reliable bright red fall color, is winter hardy, and tolerates dry and wet soils. Because of its fast growth, it requires a lot of field pruning. The fast growth and somewhat soft wood can cause breaking of branches in strong winds.

*Acer×freemanii* 'Armstrong' (not patented in the U.S.) is a fast growing spire-shaped tree having good fall color. This tree has not been hardy in the upper Midwest. Similarly, *Acer×freemanlii* 'Celzam' (U.S. Plant Pat. No. 7,279), has not been hardy in the upper Midwest.

A novel variety of maple has now been discovered, showing reliable fill color and superior winter hardiness for growth in regions such as the upper Midwest.

SUMMARY OF THE INVENTION

The novel cultivar of the invention named 'Sienna' is an *Acer×freemanii* characterized in the following manner:

1. Distinct, upright, pyramidal growth habit which is readily apparent as a young tree, and becomes broad pyramidal in the mature tree.

2. Exhibits vigorous growth.

3. Assumes an outstanding deep burgundy coloration in the fall.

4. Exhibits superior winter hardiness which is equal or superior to that of other *Acer×freemanii* cultivars. No frost cracking, sun scald or winter dieback has been observed on trees grown in Minnesota.

DETAILED DESCRIPTION OF THE INVENTION

Figure 1:
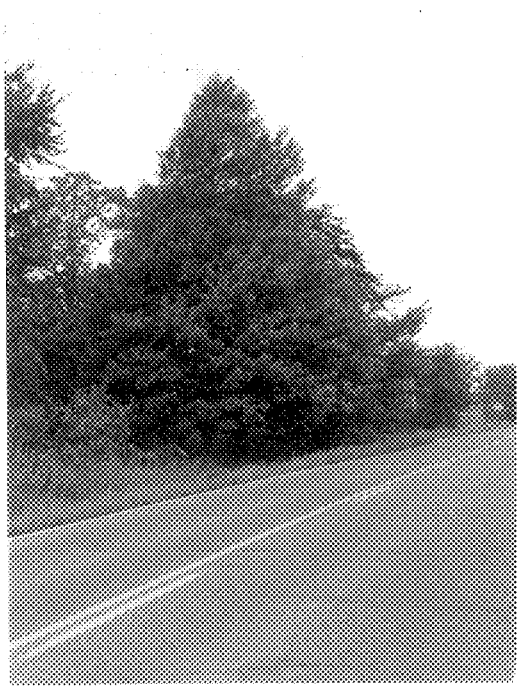
FIG. 1 is a photographic view of the mature original tree in summer.
Figure 2:
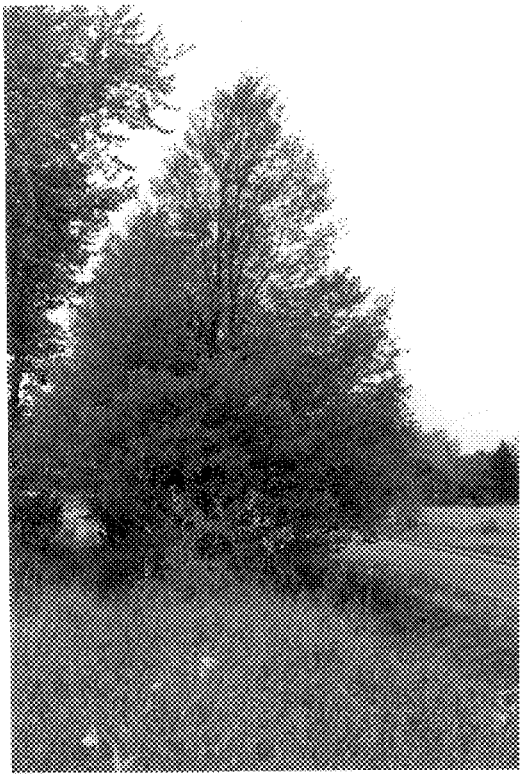
FIG. 2 is a photographic view of the mature original tree in fall.
Figure 3:
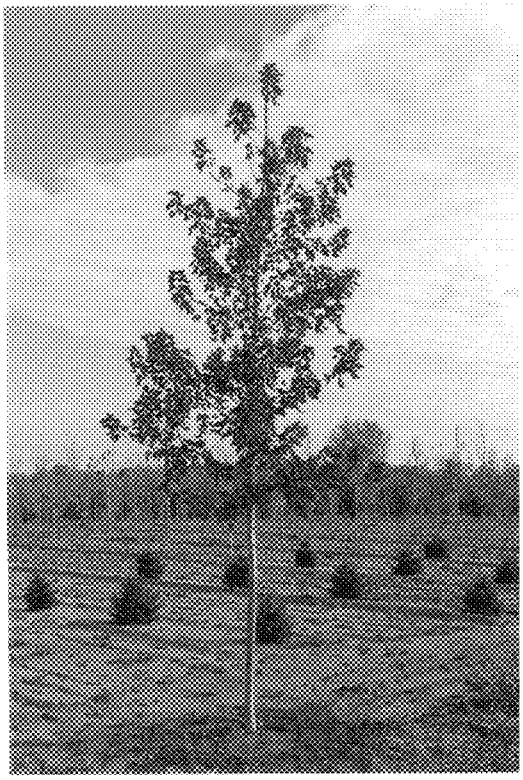
FIG. 3 is a photographic view of a propagated tree (2¼ inch caliper) in fall.
Figure 4:
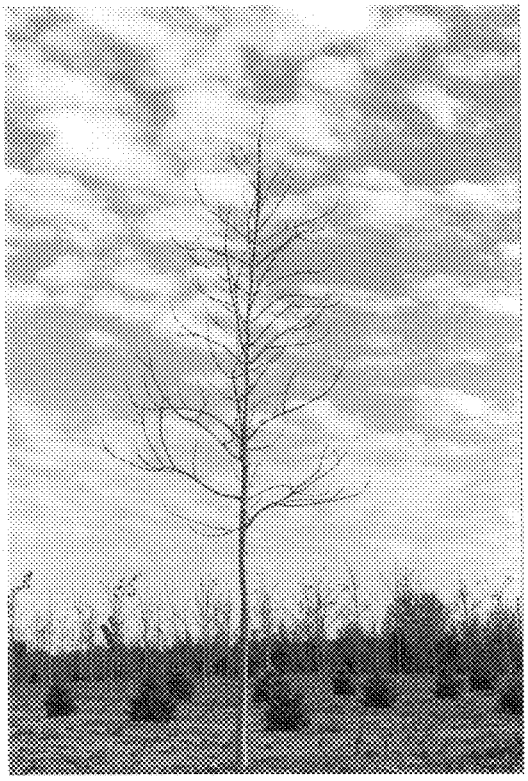
FIG. 4 is a photographic view of a propagated tree (2¼ inch caliper) showing branch structure.
Figure 5:
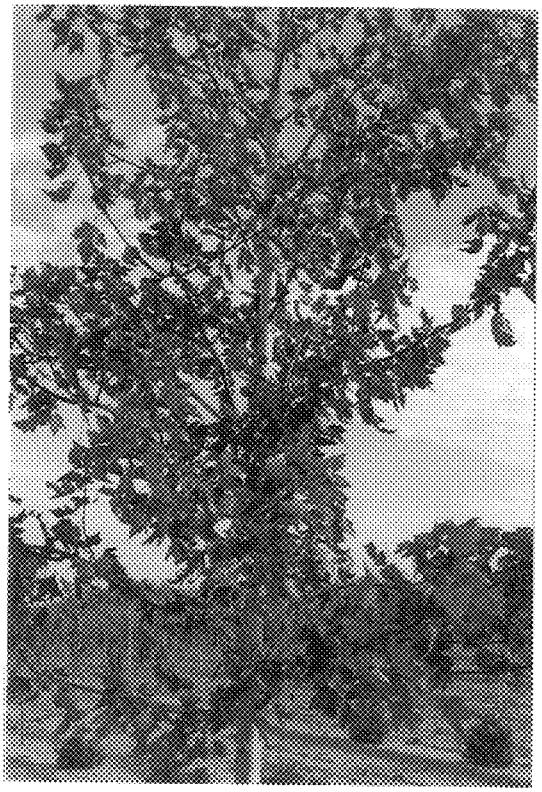
FIG. 5 is a photographic view of a propagated tree (2¼ inch caliper) showing branches.
Figure 6:
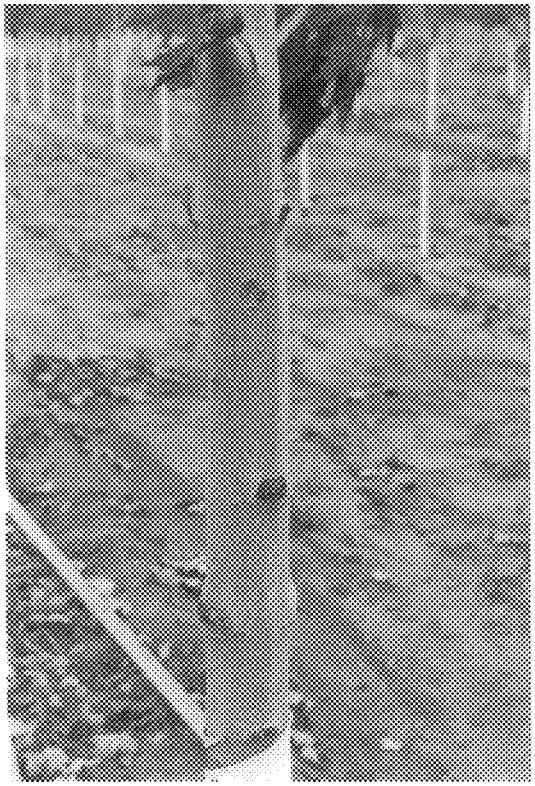
FIG. 6 is a photographic view of a propagated tree (2¼ inch caliper) showing the trunk.
Figure 7:
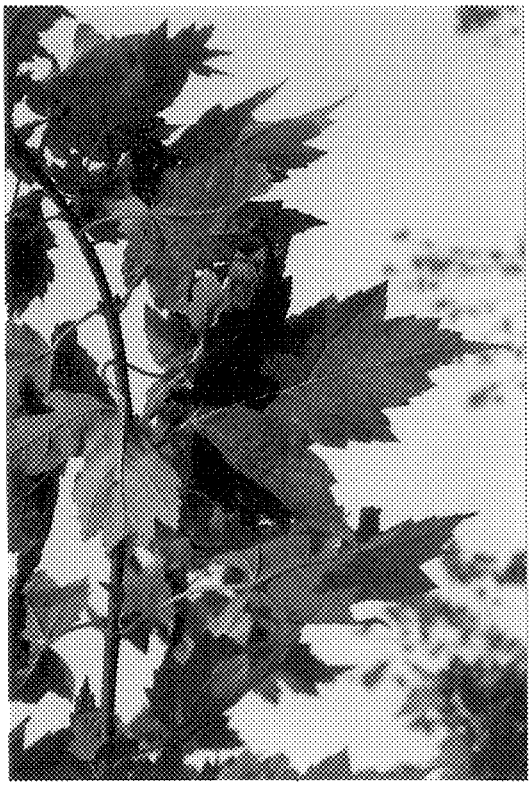
FIG. 7 is a photographic view showing a terminal branch in the fall.
Figure 8:
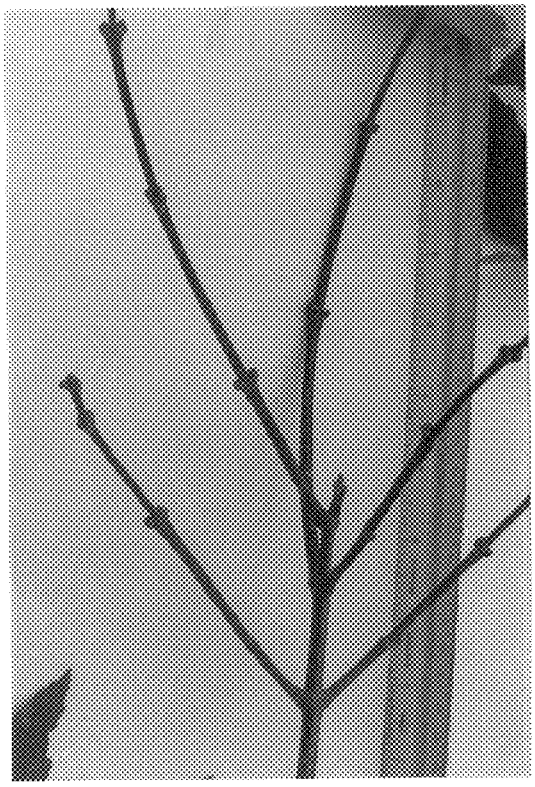
FIG. 8 is a photographic veiw showing bud set.
Figure 9:
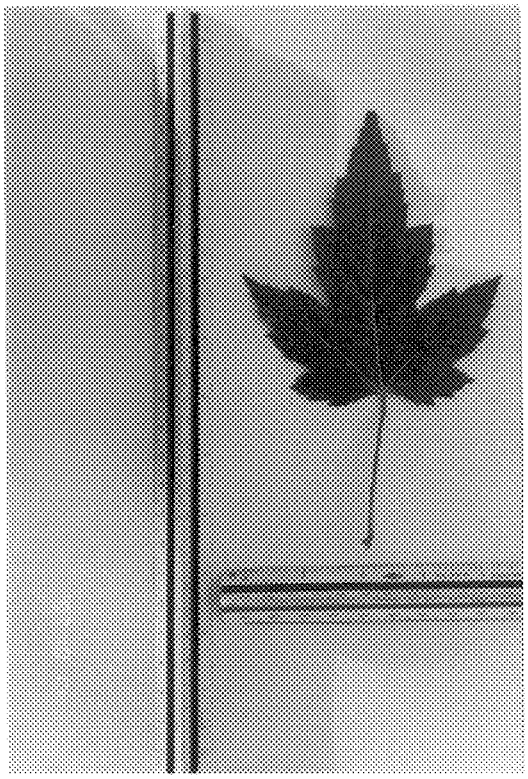
FIG. 9 is a photographic view showing the upper side of leaf.
Figure 10:
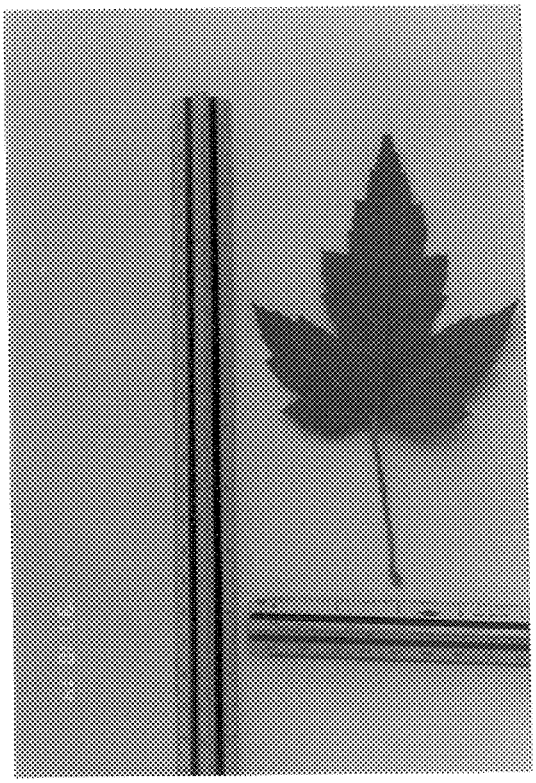
FIG. 10 is a photographic view showing the underside of leaf.
Figure 11:
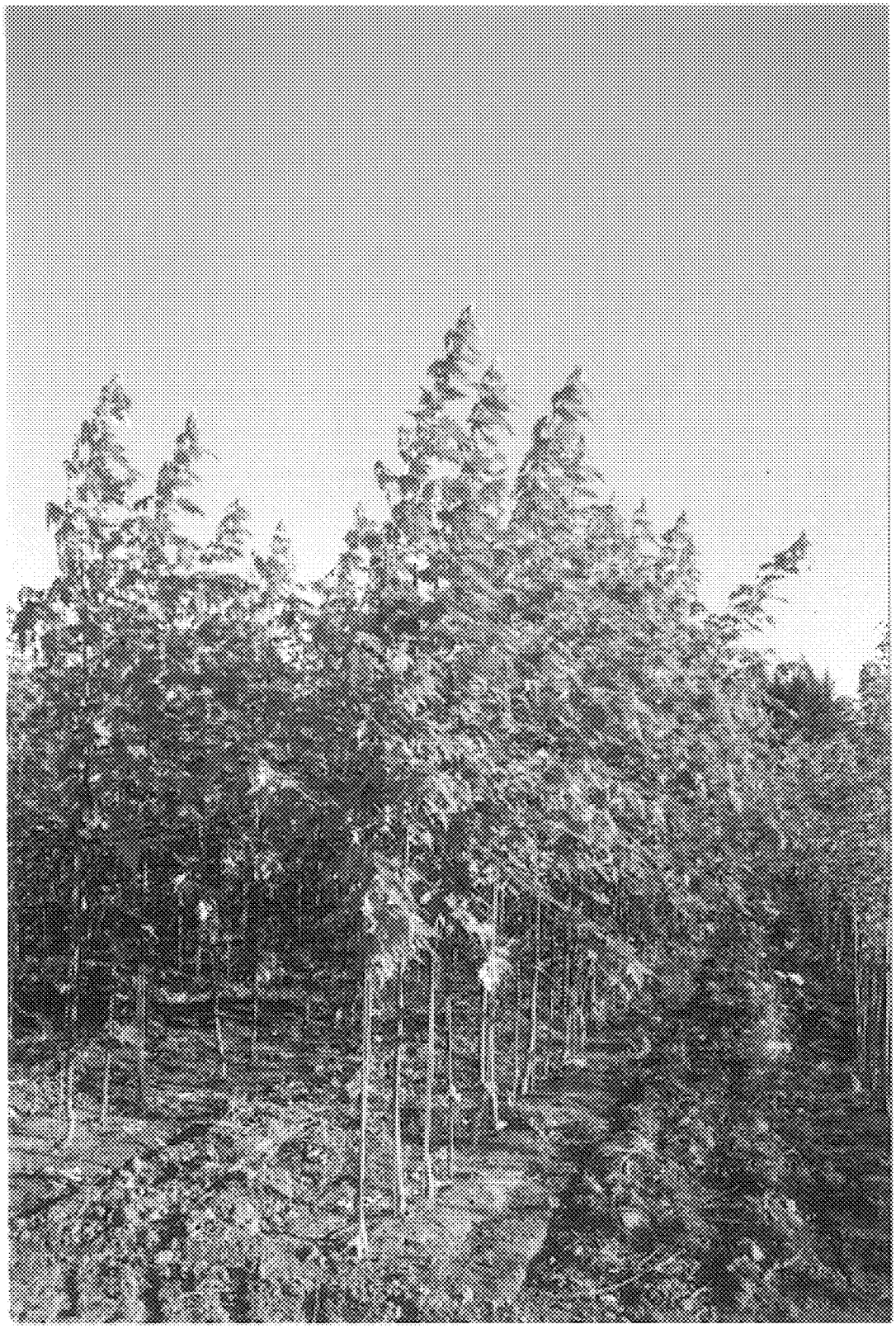
FIG. 11 is a photographic view showing propagated whip trees grown in Oregon.

The variety of *Acer×freemanii* ('Sienna') was discovered growing on an abandoned farmstead in Lake Elmo, Minn. The tree has been successfully reproduced asexually by means of rooted cuttings at Robinson Nursery in McMinnville, Oreg. The novel characteristics of the original tree are reliably transmitted to the succeeding generations.

This new cultivar of *Acer×freemanii* has a number of characteristics which make it unique compared to other *Acer×freemanii* varieties.

The following is a specific description of the instant variety. The color terminology is in reference to The Royal Horticultural Society Colour Chart.

Origin: A tree of unknown origin, found growing on an abandoned farmstead in Lake Elmo, Minn., which is believed to be an *Acer freemanii*; a hybrid of *Acer rubrum* and *Acer saccharinum*, as its characteristics are intermediate between those two species and are quite similar to those observed from controlled crosses between those two species. In particular, the leaves of 'Sienna' are more elongated (arrowhead) in shape and smaller than those of an *Acer rubrum*. The leaves are not as large, deeply lobed, or serrated as an *Acer saccharinum*, nor do they exhibit the very light gray color of the underside leaf as in *Acer saccharinum*. The branches of 'Sienna' exhibit slight looping, which is a slight down-turning of a branch a short distance from the trunk with an opposite up-turning a few feet farther along the branch. This characteristic is very prevalent on *Acer saccharinum*, but not generally present on *Acer rubrum*. The bark color of 'Sienna' is a lighter shade of gray than that of *Acer rubrum*, but not as light as that of an *Acer saccharinum*. 'Sienna' has an intermediate wood hardness that lies between that of an *Acer rubrum* and the very soft wood of an *Acer saccharinum*. Because of this, 'Sienna' is intermediate in its ability to withstand breakage.

Classification: *Acer×freemanii.*

Parentage: Unknown; believed to be a hybrid of *Acer rubrum* and *Acer saccharinum.*

Shape: Upright pyramdal with a stong central leader. The novel variety of the invention has a distinctive pyramidal shape, as compared to other types of maple, which vary from ovate ('Autumn Blaze') to columnar ('Armstrong').

Height: 2¼ inch caliper tree, 14 feet 6 inches.

Spread: 2¼ inch caliper tree; 5 feet 6 inches. At the 2½ inch size, 'Sienna' is approximately 18 inches taller and about 18 inches narrower than 'Autumn Blaze'.

Disease resistance:

*Verticillium wilt.*—The most prevalent and final disease to maple trees is *Verticillium wilt*. This disease is caused by soilborne fungi which clog the vascular tissues of the tree. Applicant has not observed any Verticillium problems on 'Sienna' in Minnesota or Oregon in fields where other types of maples have contracted the disease. Resistance to *Verticillium wilt* has been demonstrated in other Freemanii varieties.

*Anthracnose.*—Antracnose is a fungal leaf disease which can be a problem on many tree varieties. It is often most prevalent in the spring during cold wet periods of weather. Applicant has not observed Antracnose on 'Sienna' in Minnesota or Oregon in fields where other maples have contracted the disease.

*Insects.*—The most prevalent insect pest of maple trees in Minnesota are Leaf Hoppers. 'Sienna' has shown moderate resistance to Leaf Hopper infestations as compared with other types of maples.

*Climate.*—Superior winter hardiness. In general, the main cause of death to maple trees in Minnesota can be attributed to climate related problems. These include frostcrack and sunscald of the trunk caused by fluctuating temperatures; crown dieback caused by winter injury to tender branches; and leaf scorch caused by hot summer windsand saturated or droughty soil. 'Sienna' shows very good resistance to these climate and site related problems.

Flowering: Flowering characteristics have not been observed at this time. The juvenile trees grown to date (up to about 5 years of age) are grown under highly fertile conditions which forces vegetative growth and delays reproductive growth. Flowering is expected, for example, under landscaping conditions, when the tree enters reproductive growth. Flowers are expected to be characteristic of the species.

Trunk size increase. 1 inch to 1¼ inch per growing season.

Growth rate: Extremely fast. Trees field grown in Minnesota exhibit the following rate of growth:

*1st year.*—8' whips lined out in the field.

*2nd year.*—1¾ inch–2-inch caliper trees.

*3rd year.*—2½ inch–2¾ inch caliper trees.

Bark: Color gray, R.H.S. 201D. The bark is distinctly grayer than the bark of 'Autumn Blaze'. It also has numerous lenticels.

Branches: Numerous and borne uniformly along the trunk with about four to six inch spacing. Individual branches are stiffer than 'Autumn Blaze'. The bottom branches grow slightly upward, angle of attachment: 25–30 degrees from the horizontal. They are 60" in spread on a 2¼ inch caliper tree. The middle branches grow more upright at approximately a 45–50 degrees from the horizontal and are 30" wide. The top branches grow even more vertically to an angle of 50–60 degrees from the horizontal and are 18–24" in width. Spacing: 4 to 12 inches apart.

Leaves: In the mature tree, leaves are small for a maple tree with almost a cutleaf appearance. There are 3–5 lobes per leaf with a long central lobe, giving the leaves an arrowhead shape. Deciduous, opposite; simple; blades palmate and deeply 3–5 lobed. The largest leaves measure 4¼ inches in length and 4 inches in width. Average leaves are 3¾ inches in width. Small leaves are 3¼ inches in length, 3 inches in width. Margins are noticeably serrated. Color: upper side — medium green, R.H.S. 147A. Underside — light green to gray, R.H.S. 191A. Ribs and veins; Palmate.

Petiole: Slender, round, red or pink R.H.S. 174B on the upper side, light green, R.H.S. 137D on the underside. Length 1 inch to 3½ inches.

Winter buds: Vegetative, 1/16 inch long, color R.H.S. 145A.

Fall color: Rich deep burgundy, R.H.S. 183A.

Fruit: None observed.

Comparison to Autumn Blaze Maple:

*Crown.*—'Sienna' exhibits an upright pyramidal form as compared with the broad, ovate form of the 'Autumn Blaze' maple. The distinct pyramidal shape results in a lesser need for pruning than with 'Autumn Blaze'.

*Trunk.*—'Sienna' exhibits a bark color that is noticeably a light shade of gray and striated as compared with the bark color of the 'Autumn Blaze' maple.

*Fall color.*—'Sienna' exhibits a fall leaf color that is burgundy as compared with the bright red fall color of the 'Autumn Blaze' maple.

*Growth rate.*—The one year branch growth rate of 'Sienna' is approximately ⅔ that of 'Autumn Blaze'. Although the branch growth rate is slower, the caliper growth rate of the two trees is similar.

*Leaf size and shape.*—The leaves of 'Sienna' are smaller and more arrowhead in shape as compared with 'Autumn Blaze'.

*Buds.*—The terminal buds of 'Sienna' are pinkish (rosy) red with a greenish tinge as compared to the red buds of 'Autumn Blaze'. Buds in 'Sienna' are heavily concentrated towards the end of the branch on one year growth. This concentration of buds is not seen on 'Autumn Blaze'. In addition, the buds of 'Sienna' are slightly rounder than those of 'Autumn Blaze'.

*Branches.*—The branches of 'Sienna' are borne more closely together along the trunk than those of 'Autumn Blaze', and have a more stiff nature. 'Sienna' exhibits finer branching, giving the tree a more delicate appearance, although the wood is harder than that of Autumn Blaze. The branches are shorter and exhibit less looping than those of the 'Autumn Blaze' Maple. 'Sienna' branches more freely on second year growth, especially toward the terminal portion of the branch. This is a result of the large number of buds present on this portion of the branch.

Older branch growth is gray to light burgundy in color, whereas older growth of 'Autumn Blaze' is brownish red. New growth of 'Sienna' is more brown than the red color of new growth of 'Autumn Blaze'.

Lenticels on new growth are longer and spaced further apart than those of the 'Autumn Blaze'.

I claim:

1. A new and distinct variety of an *Acer×freemanii* maple tree named 'Sienna', as described and illustrated herein.

* * * * *

UNITED STATES PATENT AND TRADEMARK OFFICE

CERTIFICATE OF CORRECTION

PATENT NO. : PP11,322
DATED : April 4, 2000
INVENTOR(S) : Hanson

It is certified that error appears in the above-identified patent and that said Letters Patent is hereby corrected as shown below:

Column 1,
Line 19: "fill" should read --fall--

Column 3,
Line 42: "final" should read --fatal--
Line 46: "Verticillium" should be italicized to read --*Verticillium*--
Line 50: "Antracnose" should read --Anthracnose--
Line 54: "Antracnose" should read --Anthracnose--

Column 4,
Line 2: "windsand" should read --winds and--
Line 13: "increase." should read --increase:--
Line 35: "Deciduous" should read --Form: Deciduous--
Line 45: "1/16" should read --3/16--
Line 55: "light" should read lighter--

Signed and Sealed this

Seventeenth Day of July, 2001

*Attest:*

Nicholas P. Godici

*Attesting Officer*

NICHOLAS P. GODICI
*Acting Director of the United States Patent and Trademark Office*